US009765155B2

(12) United States Patent
Wu et al.

(10) Patent No.: US 9,765,155 B2
(45) Date of Patent: Sep. 19, 2017

(54) COVALENT DISULFIDE-LINKED DIABODIES AND USES THEREOF

(75) Inventors: Anna M. Wu, Sherman Oaks, CA (US); John E. Shively, Arcadia, CA (US); Andrew A. Raubitschek, San Marino, CA (US); Mark A. Sherman, Pasadena, CA (US); Tove Olafsen, Sherman Oaks, CA (US)

(73) Assignee: City of Hope, Duarte, CA (US)

( * ) Notice: Subject to any disclaimer, the term of this patent is extended or adjusted under 35 U.S.C. 154(b) by 160 days.

(21) Appl. No.: 13/554,306

(22) Filed: Jul. 20, 2012

(65) Prior Publication Data

US 2012/0283418 A1    Nov. 8, 2012

Related U.S. Application Data

(63) Continuation of application No. 12/788,477, filed on May 27, 2010, which is a continuation of application No. 10/690,990, filed on Oct. 23, 2003, now abandoned.

(60) Provisional application No. 60/420,271, filed on Oct. 23, 2002.

(51) Int. Cl.
*A61K 39/00*      (2006.01)
*C07K 16/46*      (2006.01)
*C07K 16/00*      (2006.01)
*C07K 16/30*      (2006.01)
*A61K 39/395*     (2006.01)

(52) U.S. Cl.
CPC .............. *C07K 16/46* (2013.01); *C07K 16/00* (2013.01); *C07K 16/3007* (2013.01); *A61K 39/39558* (2013.01); *A61K 2039/505* (2013.01); *C07K 2317/626* (2013.01); *C07K 2317/64* (2013.01); *C07K 2317/90* (2013.01); *C07K 2319/00* (2013.01)

(58) Field of Classification Search
CPC .................... A61K 2039/505; A61K 39/39558
USPC ........................................... 530/387.1, 387.3
See application file for complete search history.

(56) References Cited

U.S. PATENT DOCUMENTS

| 4,892,824 A | 1/1990 | Skaletsky |
| 4,943,525 A | 7/1990 | Dawson |
| 5,256,395 A | 10/1993 | Barbet et al. |
| 5,332,567 A | 7/1994 | Goldenberg |
| 5,376,249 A | 12/1994 | Afeyan et al. |
| 5,518,889 A | 5/1996 | Ladner et al. |
| 5,523,210 A | 6/1996 | Paulus |
| 5,534,254 A | 7/1996 | Huston et al. |
| 5,582,996 A | 12/1996 | Curtis |
| 5,591,828 A | 1/1997 | Bosslet et al. |
| 5,627,078 A | 5/1997 | Karl et al. |
| 5,637,481 A | 6/1997 | Ledbetter et al. |
| 5,688,690 A | 11/1997 | Valiante et al. |
| 5,693,477 A | 12/1997 | Cornell et al. |
| 5,705,614 A | 1/1998 | Ring |
| 5,712,136 A | 1/1998 | Wickham et al. |
| 5,747,035 A | 5/1998 | Presta et al. |
| 5,762,930 A | 6/1998 | Fanger et al. |
| 5,821,333 A | 10/1998 | Carter et al. |
| 5,830,473 A | 11/1998 | Thierfelder |
| 5,830,478 A | 11/1998 | Raso et al. |
| 5,837,242 A | 11/1998 | Holliger et al. |
| 5,840,854 A | 11/1998 | Hellstrom et al. |
| 5,844,094 A | 12/1998 | Hudson et al. |
| 5,851,527 A | 12/1998 | Hansen |
| 5,852,186 A | 12/1998 | Sodroski et al. |
| 5,861,156 A | 1/1999 | George et al. |
| 5,863,765 A | 1/1999 | Berry et al. |
| 5,869,049 A | 2/1999 | Noelle et al. |
| 5,869,620 A | 2/1999 | Whitlow et al. |
| 5,876,691 A | 3/1999 | Chester et al. |
| 5,877,291 A | 3/1999 | Mezes et al. |
| 5,932,448 A | 8/1999 | Tso et al. |
| 5,942,229 A | 8/1999 | Noelle et al. |
| 5,951,982 A | 9/1999 | Zöller et al. |

(Continued)

FOREIGN PATENT DOCUMENTS

JP    2003-504414    2/2003
WO    WO 01/05427 A1    1/2001

(Continued)

OTHER PUBLICATIONS

Olafsen et al. (Protein Eng. Des. Sel. Jan. 2004; 17 (1): 21-7).*
Huang et al. (J. Immunol. Methods. Jun. 30, 2006; 313 (1-2): 149-60).*
Sirk et al. (Bioconjug. Chem. Dec. 3, 2008; 19 (12): 2527-34).*
Liu et al. (Cancer Immunol. Immunother. Nov. 2009; 58 (11): 1761-9).*
FitzGerald et al. (Protein Eng. Oct. 1997; 10 (10): 1221-5).*
Liu et al. (Cancer Immunol Immunother. Nov. 2009; 58 (11): 1761-9).*
Nielsen et al. (Cancer Res. Nov. 15, 2000; 60 (22): 6434-40).*
Kipriyanov et al. (Int J Cancer. Aug. 31, 1998; 77(5): 763-72).*
Adams et al., "Highly specific in vivo tumor targeting by monovalent and divalent forms of 741F8 anti-c-erbB-2 single-chain Fv." *Cancer Res.* 53.17 (Sep. 1, 1993): 4026-34.

(Continued)

*Primary Examiner* — Stephen Rawlings
(74) *Attorney, Agent, or Firm* — Mintz Levin Cohn Ferris Glovsky and Popeo, P.C.

(57) ABSTRACT

The present invention provides recombinant antibody fragments which include a variable domain which has been modified by the addition of a tail sequence to its C-terminal end. The tail sequence comprises a terminal cysteine residue and an amino acid spacer and does not substantially affect the fragment's target-binding affinity. The present invention also provides pharmaceutical compositions comprising the described antibody fragments and a pharmaceutically acceptable carrier and methods of delivering an agent to cells of interest in a subject using the fragments as delivery vehicles. The invention further provides compositions comprising the described antibody fragments for the in vitro detection and measurement of target molecules which bind to the fragments and method of determining the presence or amount of such targets in a biological sample by contacting the sample with such compositions.

1 Claim, 4 Drawing Sheets

(56) References Cited

U.S. PATENT DOCUMENTS

| | | | |
|---|---|---|---|
| 5,959,083 A | 9/1999 | Bosslet et al. |
| 5,980,896 A | 11/1999 | Hellstrom et al. |
| 5,989,830 A | 11/1999 | Davis et al. |
| 5,990,275 A | 11/1999 | Whitlow et al. |
| 6,010,902 A | 1/2000 | Ledbetter et al. |
| 6,030,792 A | 2/2000 | Otterness et al. |
| 6,071,490 A | 6/2000 | Griffiths et al. |
| 6,083,763 A | 7/2000 | Balch |
| 6,096,871 A | 8/2000 | Presta et al. |
| 6,099,841 A | 8/2000 | Hillan et al. |
| 6,121,022 A | 9/2000 | Presta et al. |
| 6,150,508 A | 11/2000 | Murphy et al. |
| 6,193,966 B1 | 2/2001 | Deo et al. |
| 6,197,298 B1 | 3/2001 | Chang |
| 6,201,167 B1 | 3/2001 | Pothier |
| 6,241,961 B1 | 6/2001 | Benes et al. |
| 6,248,516 B1 | 6/2001 | Winter et al. |
| 6,284,742 B1 | 9/2001 | Curiel et al. |
| 6,294,391 B1 | 9/2001 | Badley et al. |
| 6,312,694 B1 | 11/2001 | Thorpe et al. |
| 6,342,587 B1 | 1/2002 | Barbas, III et al. |
| 6,361,774 B1 | 3/2002 | Griffiths et al. |
| 6,368,596 B1 | 4/2002 | Ghetie et al. |
| 6,387,350 B2 | 5/2002 | Goldenberg |
| 6,399,068 B1 | 6/2002 | Goldenberg |
| 6,458,933 B1 | 10/2002 | Hansen |
| 6,492,123 B1 | 12/2002 | Holliger et al. |
| 6,794,128 B2 * | 9/2004 | Marks et al. ............ 435/5 |
| 7,521,541 B2 | 4/2009 | Eigenbrot et al. |
| 7,807,778 B2 * | 10/2010 | Backer et al. ............ 530/300 |
| 7,838,637 B2 | 11/2010 | Kontermann et al. |
| 7,855,275 B2 | 12/2010 | Eigenbrot et al. |
| 8,772,459 B2 | 7/2014 | Ho et al. |
| 2002/0004215 A1 | 1/2002 | Osbourn et al. |
| 2002/0037289 A1 | 3/2002 | Thorpe et al. |
| 2002/0119096 A1 | 8/2002 | Griffiths |
| 2002/0119153 A1 | 8/2002 | Thorpe et al. |
| 2002/0132979 A1 | 9/2002 | Chen |
| 2002/0136689 A1 | 9/2002 | Reiter et al. |
| 2009/0275081 A1 | 11/2009 | Barat et al. |
| 2009/0311181 A1 | 12/2009 | Wu et al. |
| 2010/0003766 A1 | 1/2010 | Eigenbrot et al. |
| 2010/0069616 A1 | 3/2010 | Wu et al. |
| 2010/0111856 A1 | 5/2010 | Gill et al. |
| 2010/0297004 A1 | 11/2010 | Wu et al. |
| 2011/0137017 A1 | 6/2011 | Eigenbrot et al. |
| 2014/0234215 A1 | 8/2014 | Ho et al. |

FOREIGN PATENT DOCUMENTS

| | | |
|---|---|---|
| WO | WO 2007/109321 | 9/2007 |
| WO | WO 2009/032949 | 3/2009 |
| WO | WO 2011/069019 | 6/2011 |

OTHER PUBLICATIONS

Albrecht et al., "Development of anti-MUC1 di-scFvs for molecular targeting of epithelial cancers, such as breast and prostate cancers." *Q J Nucl Med Mol Imaging* 51.4 (Dec. 2007): 304-13.

Atwell et al., "scFv multimers of the anti-neuranminidase antibody NC10: length of the linker between $V_H$ and $V_L$ domains dictates precisely the transition between diabodies and triabodies," Protein Engineering, Jul. 1999, vol. 12, No. 7, pp. 597-604.

Barat et al., "Cys-diabody quantum dot conjugates (immunoQdots) for cancer marker detection." *Bioconjug Chem.* 20.8 (Aug. 19, 2009): 1474-81.

Carmichael et al., "The Crystal Structure of an Anti-CEA scFv Diabody Assembled from T84.66 scFvs in V(L)-to-V(H) Orientation: Implications for Diabody Flexibility." *J Mol. Biol.* 326.2 (Feb. 14, 2003): 341-51.

Communication pursuant to Rules 70(2) and 70a(2) EPC dated Dec. 28, 2010, received in EP Appl. No. 08799192.3, 11 pages.

Desplancq et al., "Multimerization behaviour of single chain Fv variants for the tumour-binding antibody B72.3," Protein Engineering, Aug. 1994, vol. 7, No. 8, pp. 1027-1033.

Fitzgerald et al., "Improved Tumor Targeting by Disulphide Stabilized Diabodies Expressed in Pichia Pastoris." *Protein Engineering* 10.10 (1997): 1221-1225.

Glockshuber et al., "A Comparison of Strategies to Stabilize Immunoglobulin $F_v$-Fragments." *Biochemistry* 29.6 (1990): 1362-1367.

Hollinger et al., "Diabodies: Small Bivalent and Bispecific Antibody Fragments." *Proc. Natl. Acad. Sci. USA* 90 (Jul. 1993): 6444-6448.

Hu et al., "Minibody: A Novel Engineered Anti-carcinoembryonic Antigen Antibody Fragment (Single-Chain $F_v$-$C_H^3$) Which Exhibits Rapid, High-Level Targeting of Xenografts." *Cancer Research* 56 (Jul. 1, 1996): 3055-3061.

Written Opinion dated Apr. 23, 2008, from Int'l Appl. No. PCT/US2007/007020 (WO 2007/109321).

Written Opinion dated Apr. 22, 2009, from Int'l Appl. No. PCT/US2008/075291 (WO 2009/032949).

Johnson et al., "Effector cell recruitment with novel Fv-based dual-affinity re-targeting protein leads to potent tumor cytolysis and in vivo B-cell depletion." J Mol Biol. 399.3 (Jun. 11, 2010): 436-49.

Kim et al., "Anti-CD30 diabody-drug conjugates with potent antitumor activity." *Mol Cancer Ther.* 7.8 (Aug. 2008): 2486-97.

Leung et al., "Engineering a Unique Glycosylation Site for Site-Specific Conjugation of Haptens to Antibody Fragments." *The Journal of Immunology* 154 (1995): 5919-5926.

Li et al., "Improved biodistribution and radioimmunoimaging with poly(ethylene glycol)-DOTA-conjugated anti-CEA diabody." *Bioconiug Chem.* 17.1 (Jan.-Feb. 2006): 68-76.

Li et al., "Reduction of Kidney Uptake in Radiometal Labeled Peptide Linkers Conjugated to Recombinant Antibody Fragments, Site-Specific Conjugation of DOTA-Peptides to a Cys-Diabody." *Bioconjugate Chem.* 13.5 (2002): 985-995.

McCartney et al., "Engineering disulfide-linked single-chain Fv dimers [(sFv')2] with improved solution and targeting properties: anti-digoxin 26-10 (sFv')2 and anti-c-erbB-2 741F8 (sFv')2 made by protein folding and bonded through C-terminal cysteinyl peptides." *Protein Eng.* 8.3 (Mar. 1995):301-14.

McCartney et al., Refolding of single-chain Fv with C-terminal cysteine (sFv); formation of disulfide-bonded homodimers of antic-A£'r/7B-2 and anti-digoxin sFv', Miami Short Rep., 1993, vol. 3, p. 91.

Moore et al., "Application of dual affinity retargeting molecules to achieve optimal redirected T-cell killing of B-cell lymphoma." *Blood* 117.17 (Apr. 28, 2011): 4542-51.

Olafsen et al., "Covalent Disulfide-linked Anti-CEA Diabody Allows Site-specific Conjugation and Radiolabeling for Tumor Targeting Applications." *Protein Engineering, Design & Selection* 17.1 (2004): 21-27.

Olafsen et al., "ImmunoPET imaging of B-cell lymphoma using 124l-anti-CD20 scFv dimers (diabodies)." *Protein Eng Des Sel.* 23.4 (Apr. 2010): 243-9.

Raag et al., "Single-chain Fvs." FASEB J., Jan. 1995, vol. 9, No. 1, pp. 73-80.

Rudikoff et al., *Proc. Natl. Acad. Sci. USA* 79 (1982): 1979.

Sirk et al., "Site-specific, thiol-mediated conjugation of fluorescent probes to cysteine-modified diabodies targeting CD20 or HER2." *Bioconjug Chem.* 19.12 (Dec. 2008): 2527-34.

Stimmel et al., "Site-Specific Conjugation on Serine Cysteine Variant Monoclonal Antibodies." *The Journal of Biological Chemistry* 275.39 (Sep. 29, 2000): 30445-30450.

Tai et al., "Targeting c-erbB-2 expressing tumors using single-chain Fv monomers and dimers." *Cancer Res.* 55.23Suppl (Dec. 1, 1995):5983s-59898.

Verhaar et at., "Technetium-99m Radiolabeling Using a Phage-Derived Single-Chain Fv with a C-Terminal Cysteine." *The Journal of Nuclear Medicine* 37.5 (May 1996): 868-872.

Veri et al., "Therapeutic control of B cell activation via recruitment of Fcgamma receptor llb (CD32B) inhibitory function with a novel bispecific antibody scaffold." *Arthritis Rheum.* 62.7 (Jul. 2010): 1933-43.

(56) References Cited

OTHER PUBLICATIONS

Whitlow et al., "Multivalent Fvs: characterization of single-chain Fv oligomers and preparation of a bispecific Fv," Protein Engineering, Aug. 1994, vol. 7, No. 8, pp. 1017-1026.
Wu et al., "Anti-carcinoembryonic Antigen (CEA) Diabody for Rapid Tumor Targeting and Imaging." *Tumor Targeting* 4 (1999): 47-58.
Wu et al., "High-resolution MicroPET Imaging of Carcino-Embryonic Antigen-Positive Xenografts by Using a Copper-64-Labeled Engineered Antibody Fragment," *Proc. Natl. Acad. Sci. USA*, vol. 97, No. 15, pp. 8495-8500 (2000).
Wu et al., "Tumor localization of Anti-CEA Single-Chain Fvs: Improved Targeting by Non-Covalent Dimers," *Immunotechnology*, vol. 2, pp. 21-36 (1996).
Yazaki et al., "Mammalian Expression and Hollow Fiber Bioreactor Production of Recombinant Anti-CEA Diabody and Minibody for Clinical Applications." *Journal of Immunological Methods* 253 (2001): 195-208.
Yazaki et al., "Tumor Targeting of Radiometal Labeled Anti-CEA Recombinant T84.66 Diabody and T84.66 Minibody: Comparision to Radioiodinated Fragments." *Bioconjugate Chem.* 12 (2001): 220-228.
You et al., "Expression, Purification, and Characterization of a Two Domain Carcinoembryonic Antigen Minigene (N-A3) in Pichia Pastoris:The Essential Role of the N-Domain." *Anticancer Research* 18(1998): 3193-3202.
File History, U.S. Appl. No. 10/690,990, filed Oct. 23, 2003.
File History, U.S. Appl. No. 12/537,145, filed Aug. 6, 2009.
File History, U.S. Appl. No. 12/293,860, filed Sep. 22, 2008.
File History, U.S. Appl. No. 12/676,348, filed Aug. 5, 2010.
File History, U.S. Appl. No. 12/959,340, filed Dec. 2, 2010.
File History, U.S. Appl. No. 12/363,678, filed Jan. 30, 2009.
File History, U.S. Appl. No. 12/788,477, filed May 27, 2010.
U.S. Appl. No. 10/690,990, filed Oct. 23, 2002.
U.S. Appl. No. 12/788,477, filed May 27, 2012.
City of Hope National Medical Center, "Anti-CEA antibody T84.66 humanized," Medical Imaging Law Weekly, copyright 2004, http://www.newsrx.com/newsletters/Medical-Imaginq-Law-Weekly ; dated for online publication Nov. 27, 2004.
George et al., "Radiometal labeling of recombinant proteins by a genetically engineered minimal chelation site: technetium-99m coordination by single-chain Fv antibody fusion proteins through a C-terminal cysteinyl peptide," Proc. Natl. Acad. Sci. USA, Aug. 1995, vol. 92, No. 18, pp. 8358-8362.
Gu et al., "Biological activity and microPET imaging properties of chimeric and humanized anit-prostate stem cell antigen (PSCA) antibodies," Proc Amer Assoc Cancer Res., 2005, vol. 46, Abstract #696 [Retrieved on May 14, 2012], URL: http://aacrmeetingabstracts.org/cgi/content/abstract/2005/1/164-b.
Marty et al., "Production of functionalized single-chain Fv antibody fragments binding to the ED-B domain of the B-isoform of fibronectin in *Pichia pastoris*," Protein Expression and Purification, Feb. 2001, vol. 21, Issue 1, pp. 156-164.
Neumaier et al., "Cloning of the genes for T84.66, and antibody that has a high specificity and affinity for carcinoembryonic antigen, and expression of chimeric human/mouse T84.66 genes in myeloma and Chinese hamster ovary cells," Cancer Research, 1990, vol. 50, pp. 2128-2134.
Office Action issued in U.S. Appl. No. 12/788,477, filed May 27, 2012 in 22 pages.
Preliminary Amendment filed on Dec. 21, 2011 in U.S. Appl. No. 12/788,477, filed May 27, 2012 in 9 pages.
Urva et al., "Physiologically based pharmacokinetic (PBPK) model for T.84.66, a monoclonal anti-CEA antibody," Am. Assoc. Pharm. Sci. 10 (Supp. 2), 2008, pp. 957.
All Office Actions and Responses to Office Actions for U.S. Appl. No. 12/788,477; current as of Dec. 20, 2012.
Response to Office Action filed on Dec. 21, 2012 for U.S. Appl. No. 12/788,477.
Office Action issued Apr. 22, 2011, received in U.S. Appl. No. 12/537,145.
Response to Office Action filed May 7, 2011 in U.S. Appl. No. 12/537,145.
Office Action issued Nov. 7, 2011, received in U.S. Appl. No. 12/537,145.
Response to Office Action filed Aug. 22, 2011 in U.S. Appl. No. 12/537,145.
Office Action Response filed Jun. 10, 2013 in U.S. Appl. No. 12/788,477.
Office Action dated Apr. 11, 2013, received in U.S. Appl. No. 12/788,477.
Notice of Abandonment dated Jun. 16, 2010, received in U.S. Appl. No. 10/690,990.
Request for Extension of time dated May 27, 2010, filed in U.S. Appl. No. 10/690,990.
Office Action dated Nov. 27, 2009, received in U.S. Appl. No. 10/690,990.
Office Action Response and RCE dated Aug. 10, 2009, filed in U.S. Appl. No. 10/690,990.
Final Office Action dated Feb. 9, 2009, received in U.S. Appl. No. 10/690,990.
Office Action Response dated Oct. 8, 2008, filed in U.S. Appl. No. 10/690,990.
Notice of Non-Responsive Amendment dated Sep. 22, 2008, received in U.S. Appl. No. 10/690,990.
Office Action Response dated Jun. 20, 2008, filed in U.S. Appl. No. 10/690,990.
Office Action dated Jan. 25, 2008, received in U.S. Appl. No. 10/690,990.
Office Action Response and RCE filed Oct. 18, 2007, filed in U.S. Appl. No. 10/690,990.
Notice of Appeal dated Mar. 19, 2007, filed in U.S. Appl. No. 10/690,990.
Final Office Action dated Sep. 18, 2006, received in U.S. Appl. No. 10/690,990.
Office Action Response dated Jul. 7, 2006, filed in U.S. Appl. No. 10/690,990.
Office Action dated Feb. 7, 2006, received in U.S. Appl. No. 10/690,990.
Response to Restriction Requirement filed Jan. 4, 2006, in U.S. Appl. No. 10/690,990.
Restriction Requirement dated Oct. 4, 2005, received in U.S. Appl. No. 10/690,990.
Advisory Action dated Jun. 17, 2013 received in U.S. Appl. No. 12,788,477.
Carter et al., "Engineering antibodies for imaging and therapy", Current Opinion in Biotechnology, 1997, vol. 8, pp. 449-454.
Liu et al., "Prostate-Specific Membrane Antigen Retargeted Measles Virotherapy for the Treatment of Prostate Cancer", Prostate, Jul. 1, 2009, vol. 69, No. 10, pp. 1128-1141.
Office Action dated Apr. 1, 2015 in U.S. Appl. No. 12/788,477.
Kipriyanov et al., "Bacterial Expression and Refolding of Single-Chain Fv Fragments with C-Terminal Cysteines", Cell Biophysics, vol. 26, No. 3, pp. 187-204, Jun. 1995.
Kipriyanov et al., "Recombinant Single-Chain Fv Fragments Carrying C-Terminal Cysteine Residues: Production of Bivalent and Biotinylated Miniantibodies", Molecular Immunology, vol. 31, No. 14, pp. 1047-1058, 1994.
Pack et al., "Miniantibodies: Use of Amphipathic Helices to Produce Functional, Flexibly Linked Dimeric Fv Fragments with High Avidity in *Escherichia coli*'", Biochemistry, vol. 31, No. 6, pp. 1579-1584, Feb. 18, 1992.
Begent et al., "Clinical evidence of efficient tumor targeting based on single-chain Fv antibody selected from a combinatorial library," *Nature Med.* 2: 979-984 (1996).
Behr et al., Targeting of liver metastases of colorectal cancer with IgG, F(ab')2, and Fab' anti-carcinoembryonic antigen antibodies labeled with 99mTc: the role of metabolism and kinetics, *Cancer Research (Suppl.)* 55: 5777s-5785s (1995).
Benhar et al., "Mutiations of two lysine residues in the CDR loops of a recombinant immunotoxin that reduce its sensitivity to chemical derivatization," *Bioconjug Chem* 5, 321-6 (1994).

(56) References Cited

OTHER PUBLICATIONS

Haran et al., "Domain motions in phosphoglycerate kinase: Determination of interdomain distance distributions by site-specific labeling and time0resolved fluorescence energy transfer", *Proc. Natl. Acad. Sci.* USA 89, 11764-11768 (1992).

Kreitman, et al., "Site-specific conjugation to interleukin 4 containing mutated cysteine residues produces interleukin 4-toxin conjugates with improved binding and activity", *Biochemistry* 33 (38), 11637-44, (1994).

Nikula et al., "Impact of high tyrosine fraction in complementarity determining regions: measured and predicted effects of radioiodination on IgG immunoreactivity," *Mol Immunol* 32, 865-72 (1995).

Office Action dated Feb. 4, 2013, received in U.S. Appl. No. 12/959,340.

Olafsen et al., "Cloning and sequencing of V genes from anti-osteosarcoma monoclonal antibodies TP-1 and TP-3: location of lysine residues and implications for radiolabeling," *Nucl Med Biol* 22, 765-71 (1995).

Olafsen et al., "Abundant tyrosine residues in the antigen binding site in anti-osteosarcoma monoclonal antibodies TP-1 and TP-3: Application to radiolabeling," *Acta Oncol* 35, 297-301 (1996).

Qu et al, "Carbohydrates engineered at antibody constant domains can be used for site-specific conjugation of drugs and chelates", *J. Immunol. Methods* 231, 131-144 (1998).

Rajagopalan et al., "Novel unconventional binding site in the variable region of immunoglobulins," *Proc. Natl. Acad. Sci. USA* 93: 6019-6024 (1996).

Rodwell et al., "Site-specific covalent modification of monoclonal antibodies: in vitro and in vivo evaluations," *Proc. Natl. Acad. Sci. USA* 83: 2632-2636 (1993).

Santimaria et al., "Immunoscintigraphic Detection of the ED-B Domain of Fibronectin, a Marker of Angiogenesis, in Patients with Cancer," *Clin Cancer* Res 9, 571-9 (2003).

Sundaresan et al., "Iodine-124 labeled engineered anti-CEA minibodies and diabodies allow high-contrast, antigen-specific microPET imaging of xenografts in athymic mice." (In press) *J Nucl Med*.

Waibel et al., "Stable one-step technetium-99m labeling of His-tagged recombinant proteins with a novel Tc(I)-carbonyl complex." *Nat. Biotechnol.* 17, 897-901 (1999).

Webber et al., "Preparation and characterization of a disulfide-stabilized Fv fragment of the anti-Tac antibody: Comparison with its single-chain analog," *Mol. Immunol.* 32: 249-258 (1995).

Wu et al., "Arming Antibodies: Prospects and Challenges for Immunoconjugates", Nature Biotechnology, vol. 23, No. 9, Sep. 2005, pp. 1137-1146.

Office Action dated Oct. 18, 2013 in U.S. Appl. No. 12/959,340.

Advisory Action dated Dec. 2, 2015 in U.S. Appl. No. 12/788,477.

Final Office Action dated Sep. 24, 2015 in U.S. Appl. No. 12/788,477.

Perisic, et al. Crystal structure of a diabody, a bivalent antibody fragment. Structure, Dec. 15 1994, vol. 2, pp. 1217-1226.

Advisory Action dated Dec. 2, 2015 in U.S. Appl. No. 12/788,477

Office Action dated May 19, 2016 in U.S. Appl. No. 12/788,477.

Office Action dated Aug. 30, 2016 in U.S. Appl. No. 12/788,477.

\* cited by examiner

COVALENT DISULFIDE-LINKED DIABODIES AND USES THEREOF

CROSS-REFERENCE TO RELATED APPLICATION

The present application is a continuation of U.S. patent application Ser. No. 12/788,477, filed May 27, 2010, which is a continuation of U.S. patent application Ser. No. 10/690,990, now abandoned, filed Oct. 23, 2003, which claims priority under 35 U.S.C. §119(e) to U.S. provisional patent application No. 60/420,271 filed on Oct. 23, 2002. The aforementioned priority applications are incorporated herein by reference in their entireties.

SEQUENCE LISTING

The present application is amended to include a Sequence Listing in electronic format. The Sequence Listing is provided as a file entitled SeqListing.txt, created Jul. 20, 2012, which is 13,384 bytes in size. The information in the electronic format of the Sequence Listing is incorporated herein by reference in its entirety.

GOVERNMENT RIGHTS STATEMENT

The invention described herein was made with Government support under grant numbers P01 CA 43904 from the National Institutes of Health and DAMD17-00-1-0150 from the Department of Defense. Accordingly, the United States Government has certain rights in this invention.

FIELD OF THE INVENTION

The present invention relates to recombinant antibody fragments, nucleic acids encoding such recombinant antibody fragments, and methods of using such recombinant antibody fragments, particularly for in vivo delivery of agents to specific cells of interest.

BACKGROUND OF THE INVENTION

Throughout this application, various publications are referenced. Disclosures of these publications in their entireties are hereby incorporated by reference into this application to more fully describe the state of the art to which this invention pertains. Full bibliographic citations for the references may be found listed immediately preceding the claims.

Antibodies specific for tumor-associated antigens can provide effective vehicles for in vivo delivery of agents, such as radionuclides, for detection or therapy of cancer. The potential utility of cancer-targeting antibodies can be improved by protein engineering approaches, which can be used to modify characteristics such as affinity, immunogenicity, and pharmacokinetic properties. In particular, recombinant antibody fragments have been produced with favorable characteristics, including retention of high affinity for target antigen, rapid, high level accumulation in xenografts in murine models, and quick clearance from the circulation, resulting in high tumor:normal activity ratios. Furthermore, because antibody fragments do not persist in the circulation, they are less likely to be immunogenic than intact murine or even chimeric antibodies. With the advent of humanized and human antibodies, the issue of immunogenicity of recombinant antibodies is rapidly diminishing.

Recombinant fragments such as diabodies (e.g., 55 kDa dimers of single-chain Fv fragments, which self-assemble in a cross-paired fashion as described by Holliger, et al., 1993) or minibodies (e.g., 80 kDa scFv-$C_H3$ fusion proteins as described by Hu et al., 1996)) have shown promise as in vivo imaging agents in preclinical studies when radiolabeled with single-photon emitting radionuclides such as In-111 or I-123, or positron emitters such as Cu-64 or I-124 for positron emission tomography (Sundaresan et al., In press; Wu et al. 2000). Targeting and imaging of I-123 radiolabeled single-chain Fv (scFv, 27 kDa) fragments has been demonstrated clinically, although the size and monovalency of scFv's may limit their utility (Begent, et al., 1996). Recent clinical imaging studies using I-123 radiolabled diabodies appear promising (Santimaria et al. 2003).

Most current antibody radiolabeling approaches involve conjugation to random sites on the surface of the protein. For example, standard radioiodination methods result in modification of random surface tyrosine residues. Many antibodies are highly susceptible to inactivation following iodination, presumably due to modification of key tyrosines in or near the binding site. (Nikula et al., 1995; Olafsen et al., 1996). Chemical modification of lysines located in or near the antigen-binding site could also potentially interfere with binding through sterical hindrance if a bulky group is added (Benhar et al., 1994; Olafsen et al., 1995). Alternative iodination approaches or radiometal labeling through conjugation of bifunctional chelates direct modifications to ε-amino groups of lysine residues, again randomly located on the surface of antibodies. The issue of inactivation following radiolabeling becomes more pressing as one moves to smaller and smaller antibody fragments, if equal reactivity is assumed, because the binding site(s) represent a larger proportion of the protein surface, and fewer "safe" sites for conjugation are available.

Site-specific radiolabeling approaches provide a means for both directing chemical modification to specific sites on a protein, located away from the binding site, and for controlling the stoichiometry of the reaction. Several strategies capitalize on naturally occurring moieties or structures on antibodies that can be targeted chemically. For example, the carbohydrate found on constant domains of immunoglobulins can be oxidized and conjugated with bifunctional chelates for radiometal labeling. (Rodwell, et al., 1993). In one instance, an unusual carbohydrate moiety occurring on a hypervariable loop of a kappa light chain was modified for site-specific chelation and radiometal labeling (Leung, et al., 1995). Others have exploited selective reduction of interchain disulfide bridges to enable modification using thiol-specific reagents. C-terminal cys residues on antibody Fab or Fab' fragments have been used for direct labeling using $^{99m}Tc$ (Behr, et al., 1995; Verhaar, et al., 1996). Novel approaches include the identification of a purine binding site in antibody Fv fragments, allowing specific photoaffinity labeling (Rajagopalan, et al., 1996).

More recently, genetic engineering approaches have been used to introduce specific sites for modification or radiolabeling of proteins and antibodies. Building on the above-mentioned work, glycosylation sites have been engineered into proteins to provide novel carbohydrate targets for chemical modification (Leung, et al., 1995; Qu, et al., 1998). The six-histidine tail commonly appended to recombinant proteins to provide a purification tag has been used in a novel 99mTc labeling method (Waibel, et al., 1999). Alternatively, a popular strategy has been to use site-directed mutagenesis to place cys residues on the surface of proteins to provide reactive sulfhydryl groups. This approach has been implemented by numerous groups to allow site-specific labeling of antibodies (Lyons, et al. 1990; Stimmel, et al., 2000) and other proteins (Haran, et al., 1992; Kreitman, et al., 1994).

Introduction of cys residues into engineered antibody fragments also has been used for stabilization or multimerization purposes. For example, introduction of strategically placed cys residues in the interface between the $V_H$ and $V_L$ domains of antibody Fv fragments has allowed covalent linkage and stabilization of these fragments (disulfide-stabilized Fv, or dsFv) (Glockshuber, et al., 1990; Webber, et al., 1995). Fitzgerald et al. described a disulfide bonded diabody in which cysteine residues were introduced into the $V_L/V_H$ interface for stability and demonstrated its utility for fluorescent imaging of tumors (Fitzgerald, et al., 1997). Others have appended cys residues to the C-termini of single-chain Fv fragments (scFv, formed by fusing $V_H$ and $V_L$ with a synthetic peptide linker) to allow multimerization into scFv'$_2$ fragments (Adams, et al., 1993; Kipriyanov, et al., 1995).

We have previously produced an anti-carcinoembryonic antigen (anti-CEA) diabody from the murine anti-CEA T84.66 antibody by joining $V_L$—eight amino acid linker—$V_H$. Tumor targeting, imaging, and biodistribution studies of a radiolabeled (at random sites on the protein) anti-CEA diabody demonstrated rapid tumor uptake, fast clearance from the circulation, and favorable properties for use as an imaging agent, when evaluated in nude mice bearing LS14T xenografts (Wu, et al., 1999; Yazaki et al., 2001b).

There remains a need in the art, however, for a stable, in vivo delivery vehicle that can be modified readily in specific locations without affecting the ability of the vehicle to specifically target cells of interest. There is also a continuing need for better in vitro detection methods. The invention provides a system for adding site-specific functional groups to antibody fragments that do not interfere with target binding by said fragment.

SUMMARY OF THE INVENTION

The present invention provides recombinant antibody fragments for use in in vivo delivery of agents for detection and treatment of diseases, primarily cancers. The present invention also provides recombinant antibody fragments for the in vitro detection of certain targets of interest. Preferred antibody fragments comprise at least two single chain polypeptide subunits, each subunit having a heavy-chain variable domain polypeptide sequence connected by a linker sequence to a light-chain variable domain polypeptide sequence. One of the variable domain polypeptide sequences in each subunit is modified at its C-terminal end by addition of a tail sequence. The tail sequence comprises a terminal cysteine residue and an amino acid spacer. The selection of the C-terminal end as the modification site for introduction of the tail sequence provides a location at the end of the variable region opposite the target combining site. This configuration avoids interference with antigen binding and thus, the addition of the tail sequence does not substantially affect the antibody fragment's target-binding affinity. A "target" in the context of the present invention is a molecule of interest that can bind to or complex with the antibody fragments of the present invention and includes any molecule against which an antibody can be isolated. Examples of a target include an antigen, an anti-antibody, a self antigen or a hapten. Accordingly, "target binding sites" in the context of the present invention are sites of antibody fragments that bind "targets" and include, but are not limited to, antigen binding sites.

The subunits assemble such that each heavy chain domain is bound to a light chain domain, thereby providing a specific target-binding site with each such light chain/heavy chain pairing. Moreover, in preferred embodiments of the invention, the addition of the tail sequence provides a disulfide covalent bond, or bridge, between the heavy chain variable regions or between the light chain variable regions, depending on to which variable region the tail sequence was added. Advantages of the bond include, but are not limited to, added stability and the presence of thiol groups in an internal, protected location, which then can be released when desired for site-specific chemical modification.

The present invention also provides pharmaceutical compositions comprising the described antibody fragments and a pharmaceutically acceptable carrier. The invention further provides methods of delivering an agent to cells of interest in a subject. Preferred delivery methods involve conjugating the agent to the recombinant antibody fragment and administering the conjugate to the subject under conditions permitting specific binding between the fragment and the cell of interest in the subject.

The present invention also provides in vitro diagnostic methods for detecting in a biological sample at least one target of interest. In such an diagnostic method complexes between at least one recombinant antibody fragment described herein and at least one target are detected.

Finally, it surprisingly has been found that the addition of a tail sequence having a terminal cysteine residue and an amino acid spacer provides advantages over known antibody fragment structures, including the formation of a stable disulfide bond and ease of site-specific chemical modification.

DETAILED DESCRIPTION OF THE INVENTION

Figure 1A:
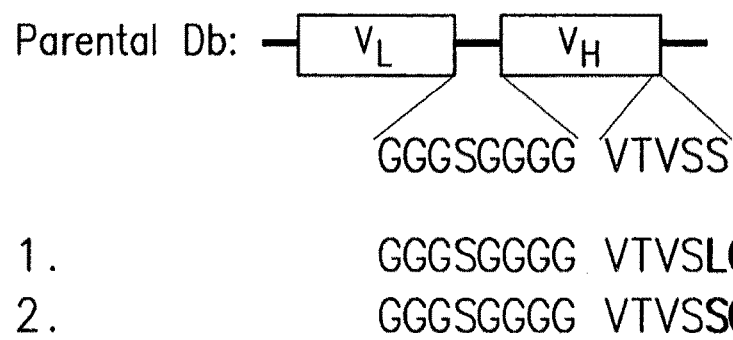
FIG. 1a shows the design of anti-CEA cys-diabodies with a parental diabody with an 8 amino acid linker sequence (SEQ ID NO: 9) between the V domains and a C-terminus 5 amino acid sequence present in the $V_H$ domain (SEQ ID NO: 10). (1) and (2) show cys-diabody variants made with the added amino acids highlighted and the cysteine residue underlined in each construct (SEQ ID NO: 2 and SEQ ID NO: 4).

The present invention provides a recombinant antibody fragment comprising at least two single chain polypeptide subunits. Each subunit comprises a heavy-chain variable domain polypeptide sequence connected by a linker sequence to a light-chain variable domain polypeptide sequence. The linker sequence is preferably a glycine sequence typically having from about 5 to about 10 glycine residues, preferably 6, 7, 8 or 9 residues and most preferably 8 residues. One of the variable domain polypeptide sequences in each subunit is modified at its C-terminal end by addition of a tail sequence. See FIG. 1.a. The tail sequence comprises an amino acid spacer and a terminal cysteine residue. The spacer, positioned between the terminal cysteine residue and the end of the sequence to which the tail is added, is preferably between 1 and about 10 residues in length, more preferably 2 to 5 residues in length, most preferably 2 residues in length. However, depending on the distance of the C-termini, a longer tail sequence might be advantageous, e.g. a tail sequence having 11, 12 or more amino acid residues. In a preferred embodiment, the residues are glycine residues. The subunits assemble such that each heavy chain domain is bound to a light chain domain, wherein each such light chain/heavy chain pairing provides a target-binding site. Following addition of the tail sequence, each target-binding site retains binding affinity substantially similar or equivalent to that of a recombinant fragment without addition of the tail sequence, as described above and illustrated by FIG. 3. "Substantially similar binding affinity" in the context of the antibody fragments according to the present invention describes an in vitro binding affinity that a person skilled in the art would consider not inferior when compared to the in vitro binding affinity of the same antibody fragment without a tail sequence.

In a preferred embodiment, the tail sequence is added to the heavy chain variable domain of each subunit and provides a disulfide covalent bond between the heavy chain variable domains. Alternatively, the tail sequence is added to the light chain variable domain of each subunit and provides a disulfide covalent bond between the light chain variable domains.

In a preferred embodiment, at least one of the target binding sites of the recombinant antibody fragment specifically binds a carcinoembryonic antigen (CEA). A preferred diabody is an anti-CEA diabody. In a preferred embodiment, at least one light chain and at least one heavy chain of the fragment correspond to a light chain variable domain and a heavy chain variable domain of the murine anti-CEA T84.66 antibody. The tail sequence preferably is added to the heavy chain variable domain of each subunit and provides a disulfide covalent bond between the heavy chain variable domains. Alternatively, the tail sequence is added to the light chain variable domain of each subunit and provides a disulfide covalent bond between the light chain variable domains.

In another preferred embodiment, the recombinant antibody fragment further comprises an agent, such as a diagnostic or therapeutic agent, conjugated to the cysteine residue of the tail sequence. This conjugation can be achieved readily by methods known in the art. The agent can be conjugated to the fragment via a thiol-specific bifunctional chelating agent or other suitable chelating agent. The agent can be, without limitation, a radionuclide label such as In-111 or I-123, a positron emitter, such as Cu-64 or I-124 or, in particular for the in vitro applications, a dye, such as a fluorescent dye for direct detection by colorimetric assays, for fluorescent detection including Fluorescence Activated Cell Sorting (FACS) or for Fluorescence Resonance Energy Transfer (FRET); a protein such as horseradish peroxidase or alkaline phosphatase, that generates a colored product with an appropriate substrate for ELISA type assays, or a luciferase that generates light upon addition of an appropriate substrate. Alternatively, the agent can be a cytotoxic agent such as a chemotherapeutic drug.

Another embodiment comprises an in vitro detection method in which an antibody fragment that has formed a complex with a target is detected via a labeled antibody or antibody fragment that is specific for a site of the fragment, attachment to which does not interfere with the fragment's ability to bind a target. Such a site is preferably the terminal LGGC or SGGC sequence.

The tail sequence for at least one of the variable domains preferably can comprise the sequence set forth in SEQ ID NO: 2. Alternatively, the tail sequence preferably can comprise the sequence set forth in SEQ ID NO: 4. The invention further provides nucleotide sequences encoding the antibody fragments described herein (SEQ ID NO: 5 and SEQ ID NO: 7).

The invention moreover provides pharmaceutical compositions which comprise a recombinant antibody fragment as described herein and a pharmaceutically acceptable carrier. These pharmaceutical compositions can be administered in accordance with the present invention as a bolus injection or infusion or by continuous infusion. Pharmaceutical carriers suitable for facilitating such means of administration are well known in the art. Examples of suitable pharmaceutical carriers are described in "Remington's Pharmaceutical Sciences" by E. W. Martin. Liquid formulations can be solutions or suspensions and can include vehicles such as suspending agents, solubilizers, surfactants, preservatives, and chelating agents.

The present invention also provides a method of delivering an agent to cells of interest in a subject which includes conjugating the agent to a recombinant antibody fragment and administering the conjugate, (or "conjugated recombinant fragment") to the subject. As described above, the recombinant antibody fragment comprises at least two single chain polypeptide subunits in which each subunit comprises a heavy-chain variable domain polypeptide sequence connected by a linker sequence to a light-chain variable domain polypeptide sequence. One of the variable domain polypeptide sequences in each subunit is modified at its C-terminal end by addition of a tail sequence comprising a terminal cysteine residue and an amino acid spacer. The spacer, positioned between the terminal cysteine residue and the end of the sequence to which the tail is added, is preferably between 1 and about 10 residues in length, most preferably about 2 residues in length. In a preferred embodiment, the residues are glycine residues. The single chain subunits assemble such that each heavy chain domain associates with a light chain domain, each such light chain/heavy chain pairing thereby providing a target-binding site. At least one target-binding site specifically binds the cells of interest.

The conjugate is then administered to the subject under conditions permitting the conjugate to specifically bind targets on the cells of interest, which in turn thereby achieves delivery of the agent to cells of interest in the subject. Methods of in vivo targeting which are suitable for delivering conjugated antibody fragments are known in the art and described in the example provided herein. The subject is preferably a human patient. The amount to be administered to a human patient can be determined readily through methods known in the art, including those based on animal data. The cells of interest are preferably cancer cells and can be, without limitation, colon cancer cells, breast cancer cells, lung cancer cells, lymphoma cells, or cells from other human malignancies and other human diseases or conditions. The agent is preferably a detectable label. In a preferred embodiment of the invention, following administration of the conjugate to the subject, the detectable label can be detected to determine the location of the cells of interest in the subject. The detectable label can be a radioisotope, a thiol-specific label, an optical or fluorescent probe, or any other suitable label known in the art. Alternatively, the agent can be a cytotoxic agent, such as a chemotherapeutic drug or radionuclide. Methods in accordance with the present invention also can be used to diagnose, without limitation, autoimmune, inflammatory, or angiogenic processes by selecting an appropriate antibody from which to derive the antibody fragment.

The invention also provides methods of detecting and quantitatively determining the concentration of a target in a biological fluid sample. In one embodiment the method comprises contacting a solid support with an excess of a certain type of antibody fragment which specifically forms a complex with a target, such as a tumor associated antigen, e.g., CEA, under conditions permitting the antibody fragments to attach to the surface of the solid support. The resulting solid support to which the antibody fragments are attached is then contacted with a biological fluid sample so that the target in the biological fluid binds to the antibody fragments and forms a target-antibody complex. The complex can be labeled with a detectable marker. Alternatively, either the target or the antibody fragments can be labeled before the formation the complex. For example, a detectable marker can be conjugated to the antibody fragments as described elsewhere herein. The complex then can be detected and quantitatively determined thereby detecting and quantitatively determining the concentration of the target in the biological fluid sample.

A biological fluid according to the present invention includes, but is not limited to tissue extract, urine, blood, serum, and phlegm. Further, the detectable marker includes but is not limited to an enzyme, biotin, a fluorophore, a chromophore, a heavy metal, a paramagnetic isotope, or a radioisotope.

Further, the invention provides a diagnostic kit comprising an antibody fragment that recognizes and binds an antibody or antibody fragment against a target; and a conjugate of a detectable label and a specific binding partner of the antibody or antibody fragment against the target. In accordance with the practice of the invention the label includes, but is not limited to, enzymes, radiolabels, chromophores and fluorescers.

In light of the preceding description, one of ordinary skill in the art can practice the invention to its fullest extent. The following example, therefore, is merely illustrative and should not be construed to limit in any way the invention as set forth in the claims which follow.

Example

In the present example, cysteine residues were introduced into an anti-CEA diabody at different locations, in order to provide specific thiol groups for subsequent chemical modification. Modified proteins carrying an added C-terminal gly-gly-cys sequence were shown to exist exclusively as a disulfide-bonded dimer. This "cys-diabody" retained high binding to CEA and demonstrated tumor targeting and biodistribution properties identical to the non-covalent diabody. Furthermore, following reduction of the disulfide bond, the cys-diabody could be chemically modified using a thiol-specific bifunctional chelating agent, to allow labeling with radiometal. Thus, the disulfide-linked cys-diabody provides a covalently linked alternative to conventional diabodies, and, following reduction, generates specific thiol groups that are readily modified chemically. This format provides a useful platform for targeting a variety of agents to cells, such as for example, CEA-positive tumors.

In order to allow site-specific radiolabeling using thiol-specific reagents, the present example describes mutant anti-CEA diabodies engineered by substitution or addition of unique cys residues. Two variants, namely a variant having the C-terminal sequence-LGGC, and a variant having the C-terminal sequence-SGGC, were found to exist as a stable disulfide-linked dimer. The former demonstrated equivalent antigen binding in vitro and tumor targeting in vivo compared to the parental diabody shown in FIG. 1.a., and had the added advantage of allowing site-specific chemical modification following reduction of the interchain disulfide bridge. SEQ ID NO: 5 represents the nucleotide sequence of the VTVS-SGGC Cys diabody used in the examples. SEQ ID NO: 6 represents the respective amino acid sequence. SEQ ID NO: 7 represents the nucleotide sequence of the VTVS-LGGC Cys diabody used in the examples. SEQ ID NO: 8 represents the respective amino acid sequence.

Materials and Methods

Design of Cysteine-Modified Diabodies (Cys Diabodies)

Figure 1B:
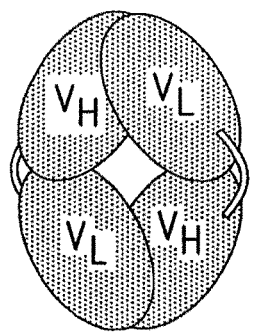
FIG. 1b is a schematic drawing of a non-covalent bound diabody.

Two variants of anti-CEA diabodies (FIG. 1, I & II; Table 1) were constructed by PCR-based mutagenesis (Quick-Change™ Site Directed Mutagenesis Kit, Strategene, LaJolla, Calif.) of the pEE12 expression vector (Lonza Biologics, Slough, UK) containing the original anti-CEA diabody constructed with an 8 amino acid glycine-serine linker (GS8) (Wu, et al., 1999). The two constructs contained a cysteine at the C-terminus of the $V_H$ and two glycines inserted in front of the cysteine as a spacer. One retained the original C-terminal sequence of the $V_H$ with GGC appended (VTVS-SGGC) and in the other, serine 113 was exchanged to a leucine (VTVS-LGGC).

Mammalian Expression, Selection and Purification $1 \times 10^7$ NS0 cells (provided by Lonza Biologics) (Galfe and Milstein, 1981) were transfected with 40 µg of linearized vector DNA by electroporation and selected in glutamine-deficient media as described (Yazaki, et al., 2001a). Clones were screened for expression by ELISA, in which the desired protein was captured either by protein L or by a recombinant CEA fragment, N-A3 (You, et al., 1998) and detected using alkaline phosphatase-conjugated goat anti-mouse Fab antibodies (Sigma, St. Louis, Mo.). Supernatants also were examined by Western blot for size analysis, using the alkaline phosphatase-conjugated goat anti-mouse Fab antibodies. The best producing clones were expanded. Cys-diabodies were purified from cell culture supernatants, using a BioCAD™ 700E chromatography system (Applied Biosystems, Foster City, Calif.) as described (Yazaki et al. 2001a). Briefly, the supernatants were treated with 5% AGI®-X8 (Bio-Rad Labs, Hercules, Calif.) overnight to remove phenol red and cell debris and then dialyzed versus 50 mM Tris-HCl, pH 7.4. Treated supernatant was loaded onto an anion exchange chromatography column (Source™ 15Q, Amersham Pharmacia Biotech AB, Uppsala, Sweden), and proteins were eluted with a NaCl gradient to 0.2 M in the presence of 50 mM HEPES, pH 7.4. Eluted fractions, containing the desired protein, were subsequently loaded onto a Ceramic Hydroxyapatite (Bio-Rad Laboratories, Hercules, Calif.) column and eluted with a KPi gradient to 0.15 M in the presence of 50 mM MES, pH 6.5. Fractions containing pure proteins were pooled and concentrated by a CENTRIPREP 10 system (Amicon Inc., Beverly, Mass.).

Elution was monitored by absorption at 280 nm. The concentration of purified protein per ml was determined by $OD_{280}$, but also by applying a small sample on protein L using known amounts of parental diabody and later cys-diabody standards quantitated by amino acid composition analysis (Wu, et al., Immunotechnology, 1996).

Characterization of Purified Cys-Diabodies

Purified proteins were analyzed by SDS-PAGE pre-cast 4-20% polyacrylamide Ready gels (Bio-Rad Laboratories under non-reducing and reducing (1 mM DTT) conditions and stained using MicrowaveBlue™ stain (Protiga Inc., Frederick, Md.). Samples were also subjected to size-exclusion HPLC on SUPERDEX 75 columns (Amersham Biosciences). Retention time was compared to a standard of parental diabody. Binding to CEA was initially assessed by ELISA as described above. Competition/Scatchard was also carried out in ELISA microtiter plates wells coated with N-A3, using a fixed concentration (1 nM) of biotinylated chimeric T84.66 antibody, and increasing concentration of non-biotinylated competitors (0.01-100 nM). Displacement was monitored with alkaline phosphatase-conjugated streptavidin (1:5000 dilution) (Jackson ImmunoResearch Labs, West Grove, Pa.) and color was developed with Phosphatase substrate tablets (Sigma, St. Louis, Mo.) dissolved in diethanolamine buffer, pH 9.8. All experiments were carried out in triplicate.

Radioiodination

70 µg of purified cys-diabody was radiolabeled with 140 µCi $Na^{131}I$ (Perkin Elmer Life Sciences, Inc., Boston, Mass.) in 0.1 phosphate buffer at pH 7.5, using 1.5 ml polypropylene tubes coated with 10 µg Iodogen (Pierce, Rockford, Ill.). Following a 5-7 min. incubation at room temperature, the sample was purified by HPLC on SUPERDEX 75 columns. Peak fractions were selected and diluted in normal saline/1% human serum albumin to prepare doses for injection. The labeling efficiency was 85%. Immunoreactivity and valency were determined by incubation of radiolabeled protein with a 20-fold excess of CEA at 37° C. for 15 min., followed by HPLC size-exclusion chromatography on a calibrated Superose 6 column (Amersham Biosciences).

Biodistribution in Tumor-Bearing Mice 7-8 week-old female athymic mice were injected subcutaneously in the flank with $10^6$ LS174T human colon carcinoma cells (ATCC #CL-188). At 7 days post inoculation, mice bearing LS174T xenografts were injected with 1 µg of $^{131}$I-labeled cys-diabody (specific activity, 1.7 µCi/µg) via the tail vein. Groups of five mice were sacrificed and dissected at 0, 2, 4, 6, and 24 h post injection. Major organs were weighed and counted in a gamma scintillation counter. Radiouptakes in organs were corrected for decay and expressed as percentage of injected dose per gram of tissue (% ID/g) and as percentage of injected dose per organ (% ID/organ). Tumor masses ranged from an average of 0.580 mg (0 h group) to 1.058 mg (24 h group). Biodistribution data are summarized as means and corresponding standard errors (sem). Animal blood curves were calculated using ADAPT II software (D'Argenio and Schumitzky, 1979) to estimate two rate constants ($k_i$) and associated amplitudes ($A_i$).

Conjugation and Radiometal Labeling of Cys-Diabodies

The VTVS-LGGC cys-diabody was reduced and conjugated with a novel bifunctional chelating agent comprised of the macrocyclic chelate DOTA (1,4,7,10-tetraazacyclododecane-1,4,7,10-tetraacetic acid), a tetrapeptide linker, and hexanevinylsulfone group for chemical attachment to thiol groups. This compound, DOTA-glycylleucylglycyl-{ε-amino-bis-1,6 hexanevinylsufone) lysine, abbreviated DOTA-GLGK-HVS, is described in greater detail elsewhere (Li, et al., 2002). VTVS-LGGC cys-diabody (2 mg in 0.5 mL PBS) was reduced by treatment with 20 µL of 20 µM tris-(carboxyethyl)phosphine (TCEP) (Pierce) in PBS for 2 h at 37° under Ar and centrifuged through a SEPHADEX G25 spin column. DOTA-GLGK-HVS, (58 µL of 20 mM in PBS) was added and the solution rotated at 10 rpm for 4 h at 25° C. The conjugate was dialyzed against 0.25 M NH40Ac, pH 7.0. Extent of modification was evaluated by isoelectric focusing gels (Li, et al., 2002).

Radiolabeling of Cys-Diabody Conjugates with Copper-64

Copper-64 (copper chloride in 0.1 N HCL; radionuclide purity >99%) was produced in a cyclotron from enriched $^{64}$Ni targets, at the Mallinckrodt Institute of Radiology, Washington University Medical Center (McCarthy, et al., 1997). DOTA-GLGK-HVS-conjugated cys-diabody (200 µg) was incubated with 7.3 mCi of $^{64}$Cu in 0.1 M $NH_4$ citrate, pH 5.5 for 1 h at 43° C. The reaction was terminated by addition of EDTA to 1 mM. Labeled protein was purified by size exclusion HPLC on a TSK2000 column (30 cm×7.5 mm I.D.; Toso-Haas; Montgomeryville, Pa.). The radiolabeling efficiency was 56% and the specific activity was 1.7 µCi/µg.

MicroPET Imaging

CEA-positive (LS174T) and CEA-negative (C6 rat glioma) xenografts were established in nude mice by subcutaneous injection of 1-2×$10^6$ cells subcutaneously into the shoulder area, 10-14 days prior to imaging. Mice were imaged using the dedicated small animal microPET scanner developed at the Crump Institute for Biological Imaging (UCLA) (Chatziioannou, et al., 1999). Mice were injected in the tail vein with 57 µCi of $^{64}$Cu-diabody. After the appropriate time had elapsed, mice were anesthetized with a 4:1 mixture of ketamine (80 mg/kg body weight) and xylazine (10 mg/kg body weight, injected intraperitoneally), placed in a prone position, and imaged using the microPET scanner with the long axis of the mouse parallel to the long axis of the scanner. Acquisition time was 56 min. (8 min. per bed position; 7 bed positions), and images were reconstructed using MAP reconstruction algorithm (Qi, et al., 1998).

Results

Expression, Purification, and Characterization of Cys-Diabodies

The cys-diabodies were expressed in the mouse myeloma cell line, NS0. The expression levels for the VTVS-SGGC and VTVS-LGGC constructs were between 5-20 µg/mL as determined by ELISA. Cultures were expanded in T flasks and supernatants collected. The VTVS-SGGC and VTVS-LGGC cys-diabodies were purified essentially as described (Yazaki, et al., 2001).

Figure 2:
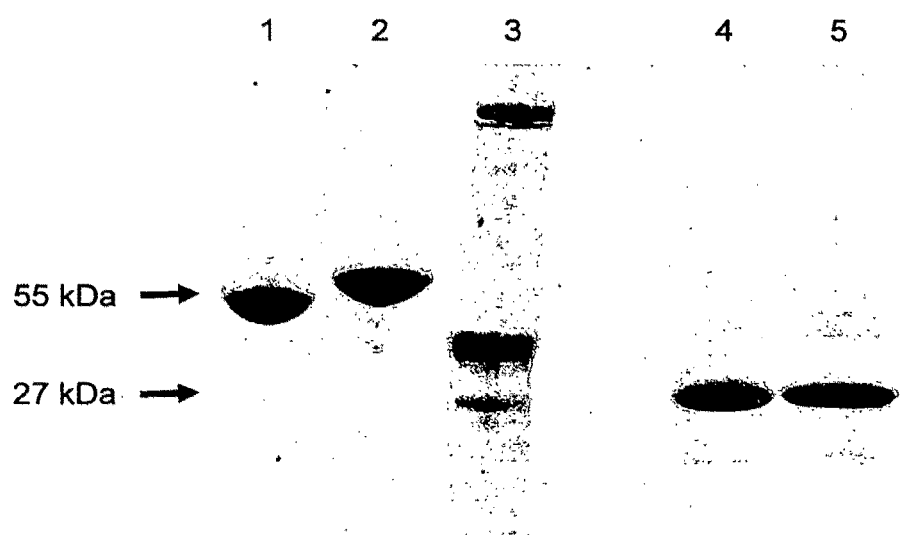
FIG. 2 shows SDS-PAGE analysis of purified antibody fragment proteins in accordance with the invention.

Analysis of the purified proteins on SDS-PAGE demonstrated that the two-step purification scheme yielded VTVS-SGGC and VTVS-LGGC diabodies that were >95% pure (FIG. 2). Under non-reducing conditions both proteins migrated as single species in the range of 55-60 kDa, with the VTVS-LGGC version exhibiting slightly lower mobility (FIG. 2, lanes 1 and 2). Under reducing conditions both proteins demonstrated the presence of the expected 25 kDa monomer (FIG. 2, lanes 4 and 5). Thus, when purified under native conditions, both of these cys-diabodies existed as essentially pure disulfide-bonded homodimers. Incorporation of a serine (polar) versus a leucine (nonpolar) residue made no difference at position 113. One of ordinary skill in the art would recognize that most other amino acid substitutions at this position would be suitable with the probable exception of cys, (which would introduce another thiol) and proline (which would restrict flexibility).

Size exclusion chromatography demonstrated that the covalently linked cys-diabody was slightly smaller than the regular diabody, as it eluted at 20.42 min. (average of 5 experiments) as opposed to 20.13 min. (average of 4 experiments) (not shown).

Figure 3:
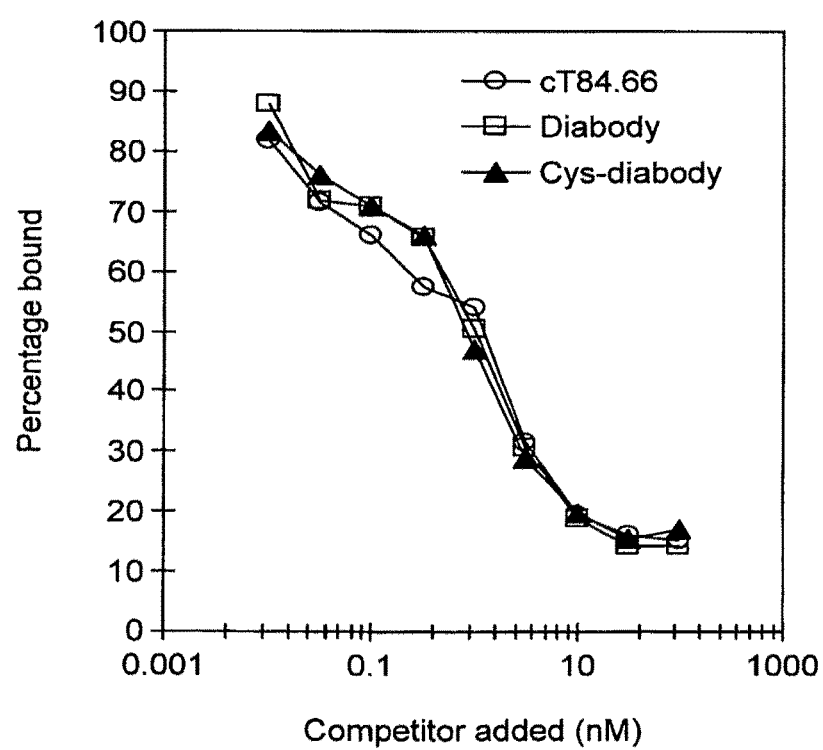
FIG. 3 shows results of a competition ELISA between an embodiment of the present invention, a known antibody, and a known antibody fragment.

The binding-activity of the cys-diabody to CEA was initially demonstrated by ELISA. Affinity was measured by competition ELISA in the presence of competitors at different concentrations. As shown in FIG. 3, by competition assay the affinities of the cys-diabody and parental diabody were essentially the same as that of the parental intact murine T84.66 monoclonal antibody.

The immunoreactivity and valency of the cys-diabody were analyzed following radioiodination by solution-phase incubation in the presence of excess CEA. Size-exclusion HPLC analysis demonstrated that 90% of the cys-diabody shifted to high molecular weight complexes indicated by two peaks, suggesting that the cys-diabody was bound to one and two CEA molecules (not shown).

In Vivo Biodistribution and Targeting

The $^{131}$I-labeled cys-diabody was assessed for its ability to target tumor in athymic mice bearing xenografts of LS174T human colon carcinoma cells. As can be seen in Table 2 the accumulation of the $^{131}$I-labeled cys-diabody reached 9.32% ID/g at 2 h and this level of localization was maintained at 4 and 6 hours post injection. Blood clearance was rapid and nearly complete by 18 h (0.55% ID/g), with the half life in the beta phase being 2.68 hrs., essentially the same as that observed with the non-covalently bound diabody (2.89 hrs.) (Yazaki et al., 2001 b). Activities in other normal organs (liver, spleen, lung, kidney) fell rapidly as well and were below 1% ID/g by 18 h. These biodistribution results were essentially identical to those observed for the parental anti-CEA diabody (Wu, et al., 1999).

In Vivo Imaging by MicroPET

Figure 4A:
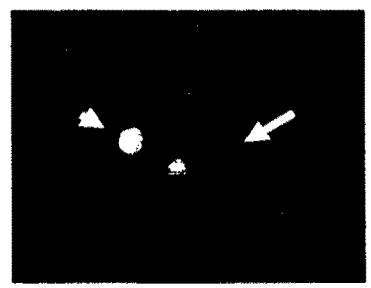
FIGS. 4a and 4b show traverse slices of serial microPET scans of a mouse bearing bilateral C6 (arrow) and LS174T (arrowhead) xenografts, injected with $^{64}$Cu cys-diabody (57 µCi) and imaged at 4 hrs (4a) and 18 hrs (4b).
Figure 4B:
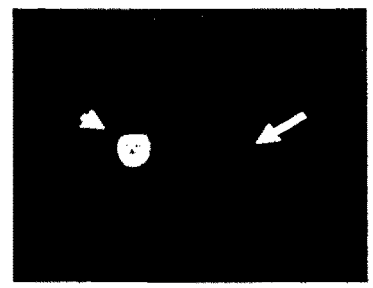

Cys-diabody was conjugated with the macrocyclic chelate DOTA using a novel peptide-hexanevinylsufone derivative described in detail elsewhere (Li, et al., 2002). This allowed efficient radiolabeling with $^{64}$Cu, a positron-emitting radionuclide with a 12.7 h half-life, well-matched to the targeting and clearance kinetics observed for diabodies in murine systems in vivo. MicroPET imaging studies were conducted on athymic mice bearing LS174T xenografts (CEA-positive human colorectal carcinoma) or C6 xenografts (CEA-negative rat glioma). Specific targeting to the CEA-positive xenograft was observed at 4 and 18 h post injection, with little evidence of activity in the CEA-negative tumor. The results are shown in FIGS. 4a and 4b. However, this particular combination of protein/chelate/radionuclide resulted in elevated liver activity (19.4% ID/g at 4 hrs) in addition to kidney activity (55.1% ID/g at 4 hrs) (Li et al. 2002).

Discussion

The present example provides the design, production and evaluation of a novel antibody format, a covalently-linked (disulfide-bonded) diabody which is referred to as the cys-diabody. Two constructs were made. The initial intent was to introduce cysteine residues into the anti-CEA diabody in order to provide specific sites for chemical modification including conjugation and radiolabeling. In course of these experiments, it was unexpectedly discovered that addition of the sequence GGC to the end of the protein resulted in a diabody in which the C-termini of the $V_L$-$V_H$ subunits came together and formed a disulfide bond. Two slightly different versions of the cys-diabody (with C-terminal sequences of LGGC or SGGC) resulted in essentially 100% formation of the disulfide linkage. This protein provides various improvements over a standard diabody, including, but without limitation, covalent linkage for greater potential stability, and the feasibility of site-specific modification following reduction of the disulfide bond and generation of free reactive thiols. Additionally, the introduced cysteine residues are essentially "protected" through the internal linkage and prevented from forming random disulfide bonds with small molecules (such as glutathione) or other sulfhydryl-containing proteins present in the cell. As a result, the cys-diabody can be obtained in higher amounts and with greater purity than might be expected for proteins containing engineered cysteine residues that are unpaired and accessible to random chemical modification and fortuitous disulfide formation.

Figure 5A:
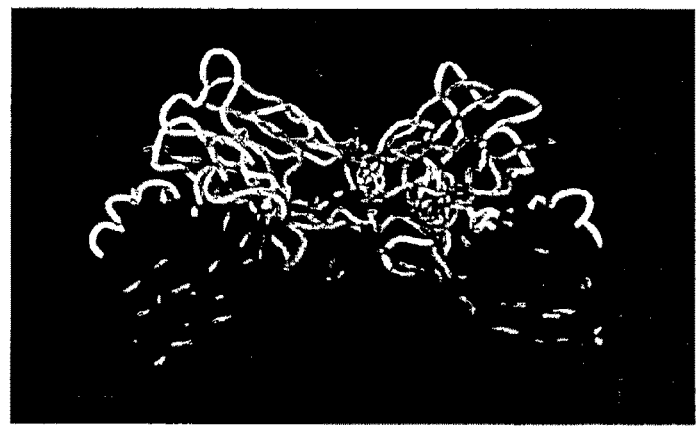
FIGS. 5a and 5b show the published crystal structure of the parental anti-CEA diabody (5a), and a model of the structure of -SGGC cys-diabody (5b) where the Fvs have been rotated to bring the C-termini close enough for disulfide bridge formation.
Figure 5B:
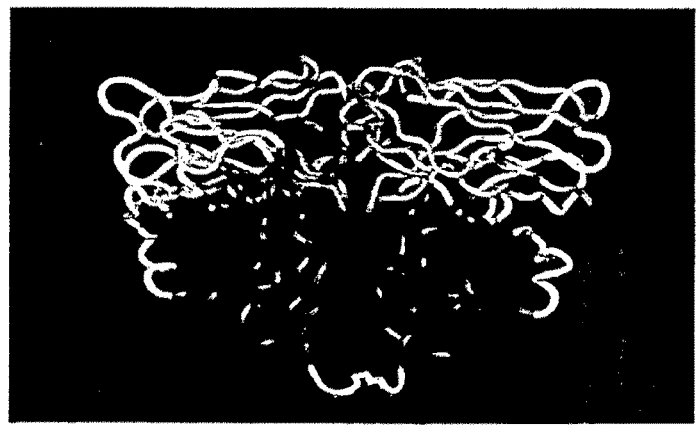

The crystal structure of the parental T84.66/GS8 diabody has recently been solved (Carmichael, et al., 2003). In the crystal, the Fv units of the diabody assumed a very compact, twisted structure, with the binding sites oriented in a skewed orientation at a tight 70° angle. The C-termini of the heavy chain variable regions (where we have appended the cys residues in the present example) are about 60 Å apart. However, the structure that was solved is likely to represent one of many conformations that the parental diabody can adopt. The fact that the cys-diabody forms with such high efficiency implies that the parental diabody is in fact quite flexible, and that the Fv domains can swivel such that the C-termini are juxtaposed. FIG. 5a shows the crystal structure of the diabody and FIG. 5b shows a model where the Fv domains have been rotated to bring the C termini close enough for disulfide bridge formation (the disulfide bridge is the light-colored loop protruding from the model in the central bottom part of the Figure). Size exclusion HPLC analysis confirms the notion that the native, non-covalent diabody is quite flexible; it elutes at an earlier retention time suggesting a larger Stokes radius. By contrast, the covalently-linked cys-diabody elutes at a later retention time, implying a more compact, more highly constrained molecule. Taken together, these results suggest that native diabody has a more open and flexible structure.

TABLE 1

Cys-diabody constructs

| | | |
|---|---|---|
| VTVS-SGGC: | 5'-GTC ACC GTC TCC TCA GGT GGA TGT-3' | (SEQ ID NO: 1) |
| | Val Thr Val Ser Ser Gly Gly Cys | (SEQ ID NO: 2) |
| VTVS-LGGC: | 5'-GTC ACC GTC TCC TTA GGT GGA TGT-3' | (SEQ ID NO: 3) |
| | Val Thr Val Ser Leu Gly Gly Cys | (SEQ ID NO: 4) |

TABLE 2

Biodistribution of $^{131}$I-labeled T84.66 cys-diabody in athymic mice bearing LS174T xenografts[a]

| | 0 | 2 | 4 | 6 | 18 | 24 |
|---|---|---|---|---|---|---|
| Organ (% ID/g) | | | | | | |
| Tumor | 2.49 ± 0.33 | 9.32 ± 1.73 | 10.02 ± 0.69 | 9.15 ± 0.77 | 6.43 ± 1.05 | 4.79 ± 1.28 |
| Blood | 36.34 ± 2.70 | 5.87 ± 0.63 | 4.04 ± 0.53 | 3.28 ± 0.27 | 0.55 ± 0.13 | 0.36 ± 0.09 |
| Liver | 8.40 ± 0.61 | 3.16 ± 0.81 | 2.66 ± 0.64 | 1.67 ± 0.27 | 0.64 ± 0.24 | 0.32 ± 0.06 |
| Spleen | 5.67 ± 0.80 | 2.54 ± 0.39 | 1.57 ± 0.20 | 1.30 ± 0.14 | 0.34 ± 0.11 | 0.19 ± 0.04 |
| Kidney | 18.58 ± 1.22 | 4.03 ± 0.57 | 2.99 ± 0.51 | 2.09 ± 0.25 | 0.47 ± 0.09 | 0.37 ± 0.04 |
| Lung | 9.90 ± 0.69 | 3.40 ± 0.48 | 2.50 ± 0.39 | 1.94 ± 0.17 | 0.46 ± 0.10 | 0.27 ± 0.07 |
| Ratios[b] | | | | | | |
| T:B | 0.07 | 1.59 | 2.48 | 2.79 | 11.69 | 13.31 |
| T:kidney | 0.13 | 2.31 | 3.35 | 4.38 | 13.68 | 12.95 |
| T:Liver Tumor | 0.30 | 2.95 | 3.77 | 5.48 | 10.05 | 14.97 |
| Tumor weight | 0.58 ± 0.28 | 0.7 ± 0.20 | 0.69 ± 0.09 | 0.63 ± 0.19 | 1.02 ± 0.54 | 1.06 ± 0.53 |

Groups of five mice were analyzed at each time point. Tumor and normal organ uptake are expressed as percent injected dose per gram (% ID/g). Table values are the means with corresponding standard errors of the means (s.e.m.). The ratios presented are the averages of the T:B, Tumor:kidney and Tumor:Liver ratios for the individual mice.
[a]Time given in hours
[b]Ratios were determined for each individual mouse, and then averages were calculated

REFERENCES

Adams, G. P., J. E. McCartney, M.-S. Tai, H. Oppermann, J. S. Huston, W. F. Stafford, M. A. Bookman, I. Fand, L. L. Houston and L. W. Weiner (1993). "Highly specific in vivo tumor targeting by monovalent and divalent forms of 741F8 anti-c-erbB-2 single-chain Fv." *Canc. Res.* 53: 4026-4034.

Begent, R. H. J., M. J. Verhaar, K. A. Chester, J. L. Casey, A. J. Green, M. P. Napier, L. D. Hope-Stone, N. Cushen, P. A. Keep, C. J. Johnson, R. E. Hawkins, A. J. W. Hilson and L. Robson (1996). "Clinical evidence of efficient tumor targeting based on single-chain Fv antibody selected from a combinatorial library." *Nature Med.* 2: 979-984.

Behr, T., W. Becker, E. Hannappel, D. M. Goldenberg and F. Wolf (1995). "Targeting of liver metastases of colorectal cancer with IgG, F(ab')2, and Fab' anti-carcinoembryonic antigen antibodies labeled with 99mTc: the role of metabolism and kinetics." *Cancer Research (Suppl.)* 55: 5777s-5785s.

Benhar, I., Brinkmann, U., Webber, K. O., and Pastan, I., "Mutations in the CDR loops of a recombinant immunotoxin that reduce its sensitivity to chemical derivatization." *Bioconjug Chem* 5 (1994), 321-6.

Carmichael, J. A., Power, B. E., Garrett, T. P., Yazaki, P. J., Shively, J. E., Raubischek, A. A., Wu, A. M., and Hudson, P. J. "The crystal structure of an anti-CEA scFv diabody assembled from T84.66 scFvs in V(L)-to-V(H) orientation: implications for diabody flexibility." (2003) *J Mol Biol* 326, 341-51.

Chatziioannou, A. F., S. R. Cherry, Y. Shao, R. W. Silverman, K. Meadors, T. H. Farquhar, M. Pedarsani and M. E. Phelps (1999). "Performance evaluation of microPET: A high-resolution lutetium oxyorthosilicate PET scanner for animal imaging." *J. Nucl. Med.* 40: 1164-1175.

D'Argenio, D. Z., and Schumitzky, A. "A program package for simulation and parameter estimation in pharmacokinetic systems." (1979) *Comput Programs Biomed* 9, 115-34.

Fitzgerald K, Holliger P, Winter G. (1997 October) "Improved tumour targeting by disulphide stabilized diabodies expressed in *Pichia pastoris.*" *Protein Eng.* 10(10):1221-5.

Galfre, G., and Milstein, C. "Preparation of monoclonal antibodies: strategies and procedures." (1981) *Methods Enzymol* 73, 3-46.

Glockshuber, R., M. Malia, I. Pfitzinger and A. Pluckthun (1990). "A comparison of strategies to stabilize immunoglobulin Fv-fragments." *Biochemistry* 29: 1362-1367.

Haran, G., E. Haas, B. K. Szpikowska and M. T. Mas (1992). "Domain motions in phosphoglycerate kinase: Determination of interdomain distance distributions by site-specific labeling and time-resolved fluorescence energy transfer." *Proc. Natl. Acad. Sci. USA* 89: 11764-11768.

Holliger, P., T. Prospero and G. Winter (1993). "'Diabodies': Small bivalent and bispecific antibody fragments." *Proc. Natl. Acad. Sci. USA* 90: 6444-6448.

Hu, S. Z., L. Shively, A. Raubitschek, M. Sherman, L. E. Williams, J. Y. C. Wong, J. E. Shively and A. M. Wu (1996). "Minibody: A novel engineered anti-carcinoembryonic antigen antibody fragment (single-chain Fv-CH3) which exhibits rapid, high-level targeting of xenografts." *Cancer Res.* 56: 3055-3061.

Kipriyanov, S. M., S. Dubel, F. Breitling, R. E. Kontermann, S. Heymann and M. Little (1995). "Bacterial expression and refolding of single-chain Fv fragments with C-terminal cysteines." *Cell Biophys* 26(3): 187-204.

Kreitman, R. J., R. K. Puri, P. Leland, B. Lee and I. Pastan (1994). "Site-specific conjugation to interleukin 4 containing mutated cysteine residues produces interleukin 4-toxin conjugates with improved binding and activity." *Biochemistry* 33(38): 11637-44.

Leung, S., M. J. Losman, S. V. Govindan, G. L. Griffiths, D. M. Goldenberg and H. J. Hansen (1995). "Engineering a unique glycosylation site for site-specific conjugation of haptens to antibody fragments." *J. Immunol.* 154: 5919-5926.

Li, L., T. Olafsen, A. L. Anderson, A. Wu, A. A. Raubitschek and J. E. Shively (2002). "Reduction of kidney uptake in radiometal labeled peptide linkers conjugated to recombinant antibody fragments. Site-specific conjugation of DOTA-peptides to a Cys-diabody." *Bioconjug Chem* 13(5): 985-95.

Lyons, A., D. J. King, R. J. Owens, G. T. Yarranton, A. Millican, N. R. Whittle and J. R. Adair (1990). "Site-specific attachment to recombinant antibodies via introduced surface cysteine residues." *Protein Engineering* 3: 703-708.

McCarthy, D. W., R. E. Shefer, R. E. Klinkowstein, L. A. Bass, W. H. Margeneau, C. S. Cutler, C. J. Anderson and M. J. Welch (1997). "Efficient production of high specific activity 64Cu using a biomedical cyclotron." *Nucl. Med. Biol.* 24: 35-43.

Nikula, T. K., Bocchia, M., Curcio, M. J., Sgouros, G., Ma, Y., Finn, R. D., and Scheinberg, D. A. "Impact of high tyrosine fraction in complementarity determining regions: measured and predicted effects of radioiodination on IgG immunoreactivity." (1995) *Mol Immunol* 32, 865-72.

Olafsen, T., Bruland, O. S., Zalutsky, M. R., and Sandlie, I. "Cloning and sequencing of V genes from anti-osteosarcoma monoclonal antibodies TP-1 and Tp-3: location of lysine residues and implications for radiolabeling." (1995) *Nucl Med Biol* 22, 765-71.

Olafsen, T., Bruland, O. S., Zalutsky, M. R., and Sandlie, I. "Abundant tyrosine resides in the antigen binding site in anti-osteosarcoma monoclonal antibodies TP-1 and TP-3: Application to radiolabeling." (1996) *Acta Oncol* 35, 297-301.

Qi, J., R. M. Leahy, S. R. Cherry, A. Chatziioannou and T. H. Farquhar (1998). "High-resolution 3D Bayesian image reconstruction using the microPET small-animal scanner." *Phys. in Med. and Biol.* 43: 1001-1013.

Qu, Z. X., R. M. Sharkey, H. J. Hansen, L. B. Shih, S. V. Govindan, J. Shen, D. M. Goldenberg and S. O. Leung (1998). "Carbohydrates engineered at antibody constant domains can be used for site-specific conjugation of drugs and chelates." *J. Immunol. Methods* 213: 131-144.

Rajagopalan, K., G. Pavlinkova, S. Levy, P. R. Pokkuluri, M. Schiffer, B. E. Haley and H. Kohler (1996). "Novel unconventional binding site in the variable region of immunoglobulins." *Proc. Natl. Acad. Sci. USA* 93: 6019-6024.

Rodwell, J. D., V. L. Alvarez, C. Lee, A. D. Lopes, J. W. F. Goers, H. D. King, H. J. Powsner and T. J. McKearn (1993). "Site-specific covalent modification of monoclonal antibodies: In vitro and in vivo evaluations." *Proc. Natl. Acad. Sci. USA* 83: 2632-2636.

Santimaria, M., Moscatelli, G., Viale, G. L., Giovannoni, L., Neri, G., Viti, F., Leprini, A., Borsi, L., Castellani, P., Zardi, L., Neri, D., and Riva, P., "Immunoscintigraphic Detection of the ED-B Domain of Fibronectin, a Marker of Angiogenesis, in Patients with Cancer." (2003) *Clin Cancer Res* 9, 571-9.

Stimmel, J. B., B. M. Merrill, L. F. Kuyper, C. P. Moxham, J. T. Hutchins, M. E. Fling and F. C. Kull, Jr. (2000). "Site-specific conjugation on serine right-arrow cysteine variant monoclonal antibodies." *J Biol Chem* 275(39): 30445-50.

Sundaresan, G., Yazaki, P. J., Shively, J. E., Finn, R. D., Larson, S. M., Raubitschek, A. A., Williams, L. E., Chatziioannou, A. F., Gambhir, S. S., and Wu, A. M. "Iodine-124 labeled engineered anti-CEA minibodies and diabodies allow high-contrast, antigen-specific microPET imaging of xenografts in athymic mice." (In press) *J Nucl Med*.

Verhaar, M. J., P. A. Keep, R. E. Hawkins, L. Robson, J. L. Casey, B. Pedley, J. A. Boden, R. H. J. Begent and K. A. Chester (1996). "Technetium-99m radiolabeling using a phage-derived single-chain Fv with a C-terminal cysteine." *J. Nucl. Med.* 37: 868-872.

Waibel, R., R. Alberto, J. Willuda, R. Finnern, R. Schibli, A. Stichelberger, A. Egli, U. Abram, J.-P. Mach, A. Pluckthun and P. A. Schubiger (1999). "Stable one-step technetium-99m labeling of His-tagged recombinant proteins with a novel Tc(I)-carbonyl complex." *Nat. Biotechnol.* 17(897-901).

Webber, K. O., Y. Reiter, U. Brinkmann, R. Kreitman and I. Pastan (1995). "Preparation and characterization of a disulfide-stabilized Fv fragment of the anti-Tac antibody: Comparison with its single-chain analog." *Mol. Immunol.* 32: 249-258.

Wu, A. M., Chen, W., Raubitschek, A., Williams, L. E., Neumaier, M., Fischer, R., Hu, S. Z., Odom-Maryon, T., Wong, J. Y., and Shively, J. E. "Tumor localization of anti-CEA single-chain Fvs: improved targeting by non-covalent dimers." (1996) *Immunotechnology* 2, 21-36.

Wu, A. M., L. E. Williams, L. Zieran, A. Padma, M. A. Sherman, G. G. Bebb, T. Odom-Maryon, J. Y. C. Wong, J. E. Shively and A. A. Raubitschek (1999). "Anti-carcinoembryonic antigen (CEA) diabody for rapid tumor targeting and imaging." *Tumor Targeting* 4: 47-58.

Wu, A. M., Yazaki, P. J., Tsai, S., Nguyen, K., Anderson, A. L., McCarthy, D. W., Welch, M. J., Shively, J. E., Williams, L. E., Raubitschek, A. A., Wong, J. Y., Toyokuni, T., Phelps, M. E., and Gambhir, S. S. "High-resolution microPET imaging of carcinoembryonic antigen-positive xenografts by using a copper-64-labeled engineered antibody fragment." (2000) *Proc Natl Acad Sci USA* 97, 8495-500.

Yazaki, P. J., L. Shively, C. Clark, C.-W. Cheung, W. Le, B. Szpikowska, J. E. Shively, A. A. Raubitschek and A. M. and Wu (2001a). "Mammalian expression and hollow fiber bioreactor production of recombinant anti-CEA diabody and minibody for clinical applications." *J. Immunol. Methods* 253: 195-208.

Yazaki, P. J., A. M. Wu, S. W. Tsai, L. E. Williams, D. N. Ikler, J. Y. Wong, J. E. Shively and A. A. Raubitschek (2001b). "Tumor targeting of radiometal labeled anti-CEA recombinant T84.66 diabody and t84.66 minibody: comparison to radioiodinated fragments." *Bioconjug Chem* 12(2): 220-8.

You, Y. H., L. J. Hefta, P. J. Yazaki, A. M. Wu and J. E. Shively (1998). "Expression, purification, and characterization of a two domain carcinoembryonic antigen minigene (N-A3) in *Pichia Pastoris*. The essential role of the N-domain." *Anticancer Res.* 18: 3193-3202.

What is claimed is:

1. A recombinant antibody or fragment thereof comprising:
   a first single chain polypeptide subunit comprising:
   a first heavy chain variable domain polypeptide sequence;
   a first light chain variable domain polypeptide sequence;
   a first linker sequence connecting the first heavy chain variable domain polypeptide sequence to the first light chain variable domain polypeptide sequence; and
   a first cysteine residue located at a first C terminus of the first single chain polypeptide subunit, wherein the first C terminus comprises a first amino acid spacer, and wherein the first cysteine is covalently attached to the first amino acid spacer; and
   a second single chain polypeptide subunit comprising:
   a second heavy chain variable domain polypeptide sequence;
   a second light chain variable domain polypeptide sequence;
   a second linker sequence connecting the second heavy chain variable domain polypeptide sequence to the second light chain variable domain polypeptide sequence; and
   a second cysteine residue located at a second C terminus of the second single chain polypeptide subunit, wherein the second C terminus comprises a second amino acid spacer, and wherein the second cysteine is covalently attached to the second amino acid spacer,
   wherein the first cysteine and second cysteine are covalently linked together; and wherein the antibody or fragment comprises a first target binding site and a second target binding site, wherein the first heavy chain variable domain polypeptide sequence and the second light chain variable domain polypeptide sequence form the first target binding site, wherein the second heavy chain variable domain polypeptide sequence and the first light chain variable domain polypeptide sequence form the second target binding site, and wherein the first and second target binding sites bind different targets;
   wherein the antibody or fragment binds to carcinoembryonic antigen (CEA); and
   wherein the recombinant antibody or fragment thereof comprises the amino acid sequence of SEQ ID NO: 6.

* * * * *

SEQUENCE LISTING

<160> NUMBER OF SEQ ID NOS: 10

<210> SEQ ID NO 1
<211> LENGTH: 24
<212> TYPE: DNA
<213> ORGANISM: Homo sapiens
<220> FEATURE:
<221> NAME/KEY: CDS

```
<222> LOCATION: (1)..(24)
<220> FEATURE:
<221> NAME/KEY: misc_feature
<222> LOCATION: (13)..(24)

<400> SEQUENCE: 1 gtc acc gtc tcc tca ggt gga tgt                                    24
Val Thr Val Ser Ser Gly Gly Cys
1               5

<210> SEQ ID NO 2
<211> LENGTH: 8
<212> TYPE: PRT
<213> ORGANISM: Homo sapiens

<400> SEQUENCE: 2

Val Thr Val Ser Ser Gly Gly Cys
1               5

<210> SEQ ID NO 3
<211> LENGTH: 24
<212> TYPE: DNA
<213> ORGANISM: Homo sapiens
<220> FEATURE:
<221> NAME/KEY: CDS
<222> LOCATION: (1)..(24)
<220> FEATURE:
<221> NAME/KEY: misc_feature
<222> LOCATION: (13)..(24)

<400> SEQUENCE: 3 gtc acc gtc tcc tta ggt gga tgt                                    24
Val Thr Val Ser Leu Gly Gly Cys
1               5

<210> SEQ ID NO 4
<211> LENGTH: 8
<212> TYPE: PRT
<213> ORGANISM: Homo sapiens

<400> SEQUENCE: 4

Val Thr Val Ser Leu Gly Gly Cys
1               5

<210> SEQ ID NO 5
<211> LENGTH: 729
<212> TYPE: DNA
<213> ORGANISM: Homo sapiens
<220> FEATURE:
<221> NAME/KEY: CDS
<222> LOCATION: (1)..(729)

<400> SEQUENCE: 5 gac att gtg ctg acc caa tct cca gct tct ttg gct gtg tct ctt ggg    48
Asp Ile Val Leu Thr Gln Ser Pro Ala Ser Leu Ala Val Ser Leu Gly
1               5                   10                  15 cag agg gcc acc atg tcc tgc aga gct ggt gaa agt gtt gat att ttt    96
Gln Arg Ala Thr Met Ser Cys Arg Ala Gly Glu Ser Val Asp Ile Phe
            20                  25                  30 ggc gtt ggg ttt ttg cac tgg tac cag cag aaa cca gga cag cca ccc   144
Gly Val Gly Phe Leu His Trp Tyr Gln Gln Lys Pro Gly Gln Pro Pro
        35                  40                  45 aaa ctc ctc atc tat cgt gca tcc aac cta gaa tct gga atc cct gtc   192
Lys Leu Leu Ile Tyr Arg Ala Ser Asn Leu Glu Ser Gly Ile Pro Val
    50                  55                  60 agg ttc agt ggc act ggg tct agg aca gac ttc acc ctc atc att gat   240
```

```
Arg Phe Ser Gly Thr Gly Ser Arg Thr Asp Phe Thr Leu Ile Ile Asp
 65                  70                  75                  80 cct gtg gag gct gat gat gtt gcc acc tat tac tgt cag caa act aat        288
Pro Val Glu Ala Asp Asp Val Ala Thr Tyr Tyr Cys Gln Gln Thr Asn
             85                  90                  95 gag gat ccg tac acg ttc gga ggg ggg acc aag ctg gaa ata aaa ggt        336
Glu Asp Pro Tyr Thr Phe Gly Gly Gly Thr Lys Leu Glu Ile Lys Gly
            100                 105                 110 gga ggc agt gga ggc ggt gga gag gtt cag ctg cag cag tcc ggg gca        384
Gly Gly Ser Gly Gly Gly Gly Glu Val Gln Leu Gln Gln Ser Gly Ala
        115                 120                 125 gag ctt gtg gag cca ggg gcc tca gtc aag ttg tcc tgc aca gct tct        432
Glu Leu Val Glu Pro Gly Ala Ser Val Lys Leu Ser Cys Thr Ala Ser
    130                 135                 140 ggc ttc aac att aaa gac acc tat atg cac tgg gtg aag cag agg cct        480
Gly Phe Asn Ile Lys Asp Thr Tyr Met His Trp Val Lys Gln Arg Pro
145                 150                 155                 160 gaa cag ggc ctg gaa tgg att gga agg att gat cct gcg aat ggt aat        528
Glu Gln Gly Leu Glu Trp Ile Gly Arg Ile Asp Pro Ala Asn Gly Asn
                165                 170                 175 agt aaa tat gtc ccg aag ttc cag ggc aag gcc act ata aca gca gac        576
Ser Lys Tyr Val Pro Lys Phe Gln Gly Lys Ala Thr Ile Thr Ala Asp
            180                 185                 190 aca tcc tcc aac aca gcc tac ctg cag ctc acc agc ctg aca tct gag        624
Thr Ser Ser Asn Thr Ala Tyr Leu Gln Leu Thr Ser Leu Thr Ser Glu
        195                 200                 205 gac act gcc gtc tat tat tgt gct ccg ttt ggt tac tac gtg tct gac        672
Asp Thr Ala Val Tyr Tyr Cys Ala Pro Phe Gly Tyr Tyr Val Ser Asp
    210                 215                 220 tat gct atg gcc tac tgg ggt caa gga acc tca gtc acc gtc tcc tca        720
Tyr Ala Met Ala Tyr Trp Gly Gln Gly Thr Ser Val Thr Val Ser Ser
225                 230                 235                 240 ggt gga tgt                                                            729
Gly Gly Cys <210> SEQ ID NO 6
<211> LENGTH: 243
<212> TYPE: PRT
<213> ORGANISM: Homo sapiens

<400> SEQUENCE: 6

Asp Ile Val Leu Thr Gln Ser Pro Ala Ser Leu Ala Val Ser Leu Gly
1               5                   10                  15

Gln Arg Ala Thr Met Ser Cys Arg Ala Gly Glu Ser Val Asp Ile Phe
            20                  25                  30

Gly Val Gly Phe Leu His Trp Tyr Gln Gln Lys Pro Gly Gln Pro Pro
        35                  40                  45

Lys Leu Leu Ile Tyr Arg Ala Ser Asn Leu Glu Ser Gly Ile Pro Val
    50                  55                  60

Arg Phe Ser Gly Thr Gly Ser Arg Thr Asp Phe Thr Leu Ile Ile Asp
65                  70                  75                  80

Pro Val Glu Ala Asp Asp Val Ala Thr Tyr Tyr Cys Gln Gln Thr Asn
            85                  90                  95

Glu Asp Pro Tyr Thr Phe Gly Gly Gly Thr Lys Leu Glu Ile Lys Gly
            100                 105                 110

Gly Gly Ser Gly Gly Gly Gly Glu Val Gln Leu Gln Gln Ser Gly Ala
        115                 120                 125

Glu Leu Val Glu Pro Gly Ala Ser Val Lys Leu Ser Cys Thr Ala Ser
```

```
                130                 135                 140
Gly Phe Asn Ile Lys Asp Thr Tyr Met His Trp Val Lys Gln Arg Pro
145                 150                 155                 160

Glu Gln Gly Leu Glu Trp Ile Gly Arg Ile Asp Pro Ala Asn Gly Asn
                165                 170                 175

Ser Lys Tyr Val Pro Lys Phe Gln Gly Lys Ala Thr Ile Thr Ala Asp
            180                 185                 190

Thr Ser Ser Asn Thr Ala Tyr Leu Gln Leu Thr Ser Leu Thr Ser Glu
        195                 200                 205

Asp Thr Ala Val Tyr Tyr Cys Ala Pro Phe Gly Tyr Tyr Val Ser Asp
    210                 215                 220

Tyr Ala Met Ala Tyr Trp Gly Gln Gly Thr Ser Val Thr Val Ser Ser
225                 230                 235                 240

Gly Gly Cys

<210> SEQ ID NO 7
<211> LENGTH: 729
<212> TYPE: DNA
<213> ORGANISM: Homo sapiens
<220> FEATURE:
<221> NAME/KEY: CDS
<222> LOCATION: (1)..(729)

<400> SEQUENCE: 7 gac att gtg ctg acc caa tct cca gct tct ttg gct gtg tct ctt ggg     48
Asp Ile Val Leu Thr Gln Ser Pro Ala Ser Leu Ala Val Ser Leu Gly
1               5                   10                  15 cag agg gcc acc atg tcc tgc aga gcc ggt gaa agt gtt gat att ttt     96
Gln Arg Ala Thr Met Ser Cys Arg Ala Gly Glu Ser Val Asp Ile Phe
            20                  25                  30 ggc gtt ggg ttt ttg cac tgg tac cag cag aaa cca gga cag cca ccc    144
Gly Val Gly Phe Leu His Trp Tyr Gln Gln Lys Pro Gly Gln Pro Pro
        35                  40                  45 aaa ctc ctc atc tat cgt gca tcc aac cta gaa tct ggg atc cct gtc    192
Lys Leu Leu Ile Tyr Arg Ala Ser Asn Leu Glu Ser Gly Ile Pro Val
    50                  55                  60 agg ttc agt ggc act ggg tct agg aca gac ttc acc ctc atc att gat    240
Arg Phe Ser Gly Thr Gly Ser Arg Thr Asp Phe Thr Leu Ile Ile Asp
65                  70                  75                  80 cct gtg gag gct gat gat gtt gcc acc tat tac tgt cag caa act aat    288
Pro Val Glu Ala Asp Asp Val Ala Thr Tyr Tyr Cys Gln Gln Thr Asn
                85                  90                  95 gag gat ccg tac acg ttc gga ggg ggg acc aag ctg gaa ata aaa ggt    336
Glu Asp Pro Tyr Thr Phe Gly Gly Gly Thr Lys Leu Glu Ile Lys Gly
            100                 105                 110 gga ggc agt gga ggc ggt gga gag gtt cag ctg cag cag tcc ggg gca    384
Gly Gly Ser Gly Gly Gly Gly Glu Val Gln Leu Gln Gln Ser Gly Ala
        115                 120                 125 gag ctt gtg gag cca ggg gcc tca gtc aag ttg tcc tgc aca gct tct    432
Glu Leu Val Glu Pro Gly Ala Ser Val Lys Leu Ser Cys Thr Ala Ser
    130                 135                 140 ggc ttc aac att aaa gac acc tat atg cac tgg gtg aag cag agg cct    480
Gly Phe Asn Ile Lys Asp Thr Tyr Met His Trp Val Lys Gln Arg Pro
145                 150                 155                 160 gaa cag ggc ctg gaa tgg att gga agg att gat cct gcg aat ggt aat    528
Glu Gln Gly Leu Glu Trp Ile Gly Arg Ile Asp Pro Ala Asn Gly Asn
                165                 170                 175 agt aaa tat gtc ccg aag ttc cag ggc aag gcc act ata aca gca gac    576
Ser Lys Tyr Val Pro Lys Phe Gln Gly Lys Ala Thr Ile Thr Ala Asp
```

```
                      180                 185                 190
aca tcc tcc aac aca gcc tac ctg cag ctc acc agc ctg aca tct gag      624
Thr Ser Ser Asn Thr Ala Tyr Leu Gln Leu Thr Ser Leu Thr Ser Glu
            195                 200                 205 gac act gcc gtc tat tat tgt gct ccg ttt ggt tac tac gtg tct gac      672
Asp Thr Ala Val Tyr Tyr Cys Ala Pro Phe Gly Tyr Tyr Val Ser Asp
210                 215                 220 tat gct atg gcc tac tgg ggt caa gga acc tca gtc acc gtc tcc tta      720
Tyr Ala Met Ala Tyr Trp Gly Gln Gly Thr Ser Val Thr Val Ser Leu
225                 230                 235                 240 ggt gga tgt                                                           729
Gly Gly Cys <210> SEQ ID NO 8
<211> LENGTH: 243
<212> TYPE: PRT
<213> ORGANISM: Homo sapiens

<400> SEQUENCE: 8

Asp Ile Val Leu Thr Gln Ser Pro Ala Ser Leu Ala Val Ser Leu Gly
1               5                   10                  15

Gln Arg Ala Thr Met Ser Cys Arg Ala Gly Glu Ser Val Asp Ile Phe
            20                  25                  30

Gly Val Gly Phe Leu His Trp Tyr Gln Gln Lys Pro Gly Gln Pro Pro
        35                  40                  45

Lys Leu Leu Ile Tyr Arg Ala Ser Asn Leu Glu Ser Gly Ile Pro Val
    50                  55                  60

Arg Phe Ser Gly Thr Gly Ser Arg Thr Asp Phe Thr Leu Ile Ile Asp
65                  70                  75                  80

Pro Val Glu Ala Asp Asp Val Ala Thr Tyr Tyr Cys Gln Gln Thr Asn
                85                  90                  95

Glu Asp Pro Tyr Thr Phe Gly Gly Thr Lys Leu Glu Ile Lys Gly Gly
            100                 105                 110

Gly Gly Ser Gly Gly Gly Gly Glu Val Gln Leu Gln Gln Ser Gly Ala
        115                 120                 125

Glu Leu Val Glu Pro Gly Ala Ser Val Lys Leu Ser Cys Thr Ala Ser
    130                 135                 140

Gly Phe Asn Ile Lys Asp Thr Tyr Met His Trp Val Lys Gln Arg Pro
145                 150                 155                 160

Glu Gln Gly Leu Glu Trp Ile Gly Arg Ile Asp Pro Ala Asn Gly Asn
                165                 170                 175

Ser Lys Tyr Val Pro Lys Phe Gln Gly Lys Ala Thr Ile Thr Ala Asp
            180                 185                 190

Thr Ser Ser Asn Thr Ala Tyr Leu Gln Leu Thr Ser Leu Thr Ser Glu
        195                 200                 205

Asp Thr Ala Val Tyr Tyr Cys Ala Pro Phe Gly Tyr Tyr Val Ser Asp
    210                 215                 220

Tyr Ala Met Ala Tyr Trp Gly Gln Gly Thr Ser Val Thr Val Ser Leu
225                 230                 235                 240

Gly Gly Cys

<210> SEQ ID NO 9
<211> LENGTH: 8
<212> TYPE: PRT
<213> ORGANISM: Homo sapiens

<400> SEQUENCE: 9
```

```
Gly Gly Gly Ser Gly Gly Gly Gly
1               5

<210> SEQ ID NO 10
<211> LENGTH: 5
<212> TYPE: PRT
<213> ORGANISM: Homo sapiens

<400> SEQUENCE: 10

Val Thr Val Ser Ser
1               5
```